US012778999B2

(12) United States Patent
Berard et al.

(10) Patent No.: US 12,778,999 B2

(45) Date of Patent: Nov. 3, 2026

(54) **USE OF A POLAR EXTRACT OF *SKELETONEMA* IN PHOTODYNAMIC THERAPY**

(71) Applicants: IFREMER, Plouzane (FR); CENTRE NATIONAL DE LA RECHERCHE SCIENTIFIQUE (CNRS), Paris (FR); CHU NANTES, Nantes (FR); UNIVERSITÉ DE LIMOGES, Limoges (FR); UNIVERSITÉ DE LA ROCHELLE, La Rochelle (FR)

(72) Inventors: Jean-Baptiste Berard, Reze (FR); Louise Lefoulon, Nantes (FR); Laurent Picot, Saint Médard d'Aunis (FR); Tan-Sothea Ouk, Sereilhac (FR); Naïma Saad, Rilhac Rancon (FR); Cornelia Landolt, Sereilhac (FR); Karine Grenier, Limoges (FR); Vincent Sol, Limoges (FR)

(73) Assignees: IFREMER, Plouzane (FR); CENTRE NATIONAL DE LA RECHERCHE SCIENTIFIQUE (CNRS), Paris (FR); CHU NANTES, Nantes (FR); UNIVERSITÉ DE LIMOGES, Limoges (FR); UNIVERSITÉ DE LA ROCHELLE, La, Rochelle (FR)

( * ) Notice: Subject to any disclaimer, the term of this patent is extended or adjusted under 35 U.S.C. 154(b) by 945 days.

(21) Appl. No.: 17/918,751

(22) PCT Filed: Apr. 13, 2021

(86) PCT No.: PCT/EP2021/059545

§ 371 (c)(1),
(2) Date: Oct. 13, 2022

(87) PCT Pub. No.: WO2021/209441

PCT Pub. Date: Oct. 21, 2021

(65) Prior Publication Data

US 2023/0241142 A1 Aug. 3, 2023

(30) Foreign Application Priority Data

Apr. 14, 2020 (FR) ...................................... 2003712

(51) Int. Cl.

| | |
|---|---|
| ***A61K 36/02*** | (2006.01) |
| ***A61K 8/9706*** | (2017.01) |
| ***A61K 9/00*** | (2006.01) |
| ***A61K 41/00*** | (2020.01) |
| ***A61P 17/10*** | (2006.01) |
| ***A61Q 19/00*** | (2006.01) |

(52) U.S. Cl.

CPC ............ *A61K 36/02* (2013.01); *A61K 8/9706* (2017.08); *A61K 9/0014* (2013.01); *A61K 41/0057* (2013.01); *A61P 17/10* (2018.01); *A61Q 19/008* (2013.01); *A61K 2236/333* (2013.01)

(58) Field of Classification Search

CPC ...................................................... A61K 36/02

See application file for complete search history.

(56) References Cited

U.S. PATENT DOCUMENTS

| | | | | |
|---|---|---|---|---|
| 5,330,741 | A | 7/1994 | Smith et al. | |
| 6,447,782 | B1 * | 9/2002 | Viron ..................... | A61K 35/68 424/78.05 |
| 2022/0249355 | A1 | 8/2022 | Fousse et al. | |

FOREIGN PATENT DOCUMENTS

| | | | |
|---|---|---|---|
| EP | 1755676 | B1 | 11/2012 |
| EP | 2152259 | B1 | 7/2013 |
| EP | 3082788 | B1 | 11/2018 |
| FR | 2791568 | | 10/2000 |
| JP | 2004532890 | A | 10/2004 |
| JP | 2007522137 | A | 8/2007 |
| KR | 20160015450 | A | 2/2016 |
| KR | 101620577 | B1 | 5/2016 |
| WO | 00/13660 | | 3/2000 |
| WO | 0059466 | A1 | 10/2000 |
| WO | 02098882 | A1 | 12/2002 |
| WO | 2005074987 | A1 | 8/2005 |
| WO | 2020221971 | A1 | 11/2020 |

OTHER PUBLICATIONS

Viron, et al.. WO-0013660-A1 (Mar. 16, 2000) (Machine Translation) retrieved on Jun. 17, 25 (Year: 2000).*

International Search Report for PCT/EP2021/059545, mailed Jun. 14, 2021, 7 pages.

Written Opinion of the ISA for PCT/EP2021/059545, mailed Jun. 14, 2021, 6 pages.

Sushanth et al., "Antioxidant and antimicrobial activities in the four species of marine microalgae isolated from Arabian Sea of Karnataka Coast", Indian Journal of Marine Sciences, vol. 44, No. 1, Dec. 31, 2014, pp. 69-75

Terekhova et al., "Influence of extrametabolites of marine microalgae on reproduction of the bacterium Listeria monocytogenes", Biologiya Morya, vol. 35, No. 4, Jun. 30, 2009, pp. 306-309.

Gonzalez-Davis et al., "Bioprospection of Microalgae and Cyanobacteria as Biocontrol Agents Against Vibrio campbellii and Their Use in White Shrimp Litopenaeus vannamei Culture", Journal of the World Aquaculture, vol. 43, No. 3, Jun. 2012, pp. 387-399.

Naviner et al., "Antibacterial activity of the marine diatom Skeletonema costatum against aquacultural pathogens", Aquaculture, vol. 174, No. 1-2, Apr. 1999, pp. 15-24. .

(Continued)

*Primary Examiner* — Qiuwen Mi

(74) *Attorney, Agent, or Firm* — NIXON & VANDERHYE

(57) ABSTRACT

Disclosed is a dermatological composition including at least one polar extract of an alga of the *Skeletonema* genus or a photosensitizer derived therefrom, for the treatment of acne or bacterial infections; as well as a process for decontaminating a surface using a polar extract of an alga of the *Skeletonema* genus or a photosensitizer derived therefrom.

15 Claims, No Drawings

(56) References Cited

OTHER PUBLICATIONS

Kim, Jung Eun, et al. "Pilot study on photodynamic therapy for acne using chlorophyll: Evaluator-blinded, split-face study." Journal of Dermatological Treatment, vol. 23, No. 1, 2012, pp. 35-36.
Office Action and Search Report, issued in Chinese Patent Application No. 202180028034 dated May 30, 2025.
Zapata, M, et al. "Cg HPLC Phytoplankton Pigment Analysis." Marine Ecology Progress Series, vol. 195, 2000, pp. 29-45.
Bingyi, "Complete Guide to Cosmetic Chemistry and Process Technology", vol. 1, China Light Industry Press, Jan. 31, 2000, p. 675 (Total No. of pages with English translation: 6).
Mingqing, "Pain Measurement and Free Radical Scavenging for Analgesia", Henan Science and Technology Press, Oct. 31, 2012, p. 7 (Total No. of pages with English translation: 6).
Office Action, issued in Chinese Patent Application No. 202180028034 dated Jan. 31, 2026.
Ping et al., "Low-level Laser Therapy Clinical Application and Progress (Part 2)", Jul. 31, 2017, China Science and Technology Press, pp. 32-133 (Total No. of pages with English translation: 8).

* cited by examiner

USE OF A POLAR EXTRACT OF *SKELETONEMA* IN PHOTODYNAMIC THERAPY

This application is the U.S. national phase of International Application No. PCT/EP2021/059545 filed Apr. 13, 2021, which designated the U.S. and claims the priority of the French patent application FR20/03712 filed on Apr. 14, 2020, the entire contents of each of which are hereby incorporated herein by reference.

BACKGROUND OF THE INVENTION

Field of the Invention

The present invention concerns a composition for use in photodynamic therapy (PDT), especially to treat skin disorders such as acne.

Description of the Related Art

Acne is associated with a sebum sebaceous glands over-secretion, which leads to clogging of the skin pores. The lesions caused can then be complicated by inflammation, which results from bacterial proliferation in the sebum associated with Cutibacterium *acnes, Staphylococcus aureus, Staphylococcus epidermidis, Staphylococcus pyogenes, Streptococcus agalactiae* or *Acarus folliculorum.*

During puberty, acne begins when the sebaceous glands mature due to their hormonal stimulation by androgens. In adults, acne is the result of stimulation of the sebaceous glands with parallel poor sebum secretion due to make-up or an increase in the synthesis of adrenal cortical hormone due to stress.

The basic concept of photodynamic therapy (PhotoDynamic Therapy; PDT) consists of the light exposure of a photosensitizer resulting in the production of singlet oxygen and other reactive oxygen species (R.O.S), which lead to the death of nearby organisms (bacteria causes inflammation in acne).

In this acne-associated PDT, the photosensitizer is applied topically to the skin surface. It is then absorbed at the level of the sebaceous gland. The area to be treated is then illuminated by means of a laser or pulsed light, which illumination allows the activation of the photosensitizer and the genesis of singlet oxygen and R.O.S. The presence of singlet oxygen, which constitutes a hyper-reactive chemical species, leads to the death of bacteria proliferating in the pores of the skin and localized desquamation of the skin allowing the clogged pores to be freed.

Examples of acne treatment by photodynamic therapies are disclosed in European patents EP 1 755 676 B1, EP 2 152 259 B1, or EP 3 082 788 B1.

To be efficient, the photosensitizer, when not activated in the absence of photostimulation, must be stable in vivo and exhibit a strong photoreactivity after illumination.

Now it is important that the photosensitizer preserves the skin cells as much as possible and does not increase the inflammation resulting from acne.

SUMMARY OF THE INVENTION

The inventors have now demonstrated that a polar extract of *Skeletonema marinoï* simultaneously exhibits the characteristics of a photosensitizer, of an anti-inflammatory and of a lipogenesis inhibitor.

Alga need light to grow and reproduce. To do their photosynthesis, they absorb light thanks to the pigments present in their chloroplasts. They thus produce dioxygen and thus transform light energy to make their matter.

Obviously, the compounds of *Skeletonema marinoï* involved in photosynthesis have particularly interesting properties, especially for the treatment of acne.

Consequently, a first object relates to a composition for photodynamic treatment (PDT) comprising at least one polar extract of an alga of the *Skeletonema* genus or a photosensitizer derived therefrom.

Preferably, this composition is a dermatological composition.

Advantageously, this composition may also aim to prevent and/or treat acne in a subject by topical application of the composition to a skin surface of the subject in combination with a light exposure of this skin surface for allowing the photosensitizer activation.

More broadly, this composition may be aimed to prevent and/or treat a bacterial infection in a subject by the topical application of the composition to an epithelium surface of the subject in combination with a light exposure of this epithelium surface for allowing the photosensitizer activation.

A second object relates to a photodynamic treatment method, which includes the steps of:

1) topical application to an epithelium surface of a subject of a therapeutically effective amount of a composition as described above; and
2) light exposure of this epithelium surface for allowing the photosensitizer activation.

Advantageously, the photodynamic treatment aims to prevent and/or treat acne in a subject.

Still advantageously, the photodynamic treatment aims to prevent and/or to treat a bacterial infection in a subject.

A third object of the invention relates to a cosmetic method with a view to eliminating skin imperfections, such as blackheads, comprising the steps of:

1) topical application to an epithelium surface of a subject of an effective amount of a composition as described above; and
2) light exposure of this epithelium surface for allowing the photosensitizer activation.

A fourth object of the invention relates to a kit intended for photodynamic treatment, which comprises:

1) a composition as described previously; and
2) a light source.

A fifth object of the invention relates to a method for decontaminating a surface, which method comprises at least the steps of:

1) application of an effective amount of at least one polar extract of an alga of the *Skeletonema* genus or of a photosensitizer derived therefrom; and
2) light exposure of this surface for allowing the photosensitizer activation.

Advantageously, this method is used in hospital hygiene. In this context, the surface to be decontaminated is a medical devices, prostheses or implants surface.

Still advantageously, this method is used in the food industry and the surface to be decontaminated is a food surface (meat, fish, etc.), a metal surface (machine, work surface, etc.), a floor or even a wall.

Sixth object of the invention relates to a method for the photo-coagulation of a subject wound, which method comprises at least the steps of:

1) applying an effective amount of at least one polar extract of an alga of the *Skeletonema* genus or a photosensitizer derived therefrom to the subject wound surface; and
2) light exposure of this surface for allowing the photosensitizer activation.

DESCRIPTION OF THE PREFERRED EMBODIMENTS

Alga of the *Skeletonema* genus are single-celled alga that are also diatoms (Bacillariophyta).

By way of example of such algae, mention may be made in particular of *Skeletonema ardens, Skeletonema barbadense, Skeletonema costatum, Skeletonema cylindraceum, Skeletonema denticulatum, Skeletonema dohrnii, Skeletonema grethae, Skeletonema grevillei, Skeletonema japonicum, Skeletonema marinoi, Skeletonema mediterraneum, Skeletonema menzelii, Skeletonema mirabile, Skeletonema potamos, Skeletonema probabile, Skeletonema pseudocostatum, Skeletonema simbirskianum Skeletonema subsalum, Skeletonema tropicum, Skeletonema utriculosa* and *Skeletonema ventricosum.*

Preferably, the alga of the *Skeletonema* genus is chosen from the group comprising *Skeletonema costatum, Skeletonema grethae, Skeletonema marinoi, Skeletonema menzellii* and *Skeletonema subsalsum.*

In a particularly preferred embodiment, the alga of the *Skeletonema* genus corresponds to *Skeletonema marinoï* or *Skeletonema grethae*, and more specifically to *Skeletonema marinoï*, which is a relatively common species in the Atlantic (it is often the major species of coastal waters in the Atlantic). The cells of this species remain attached to each other after cell divisions. Also, the alga of this species come in the form of chains of 3 to 15 cells.

"Polar extract of an alga of the *Skeletonema* genus" refers to a composition obtained by an extraction carried out on an alga of the *Skeletonema* genus with a polar solvent.

"Polar solvent" means a solvent made up of molecules having a dipole moment. This polar solvent can be protic or aprotic depending on whether or not it is able to release acidic H+ ions.

Examples of polar aprotic solvents include ketones (e.g. acetone or butanone), sulfoxides (e.g. DMSO), N,N disubstituted amides (N,N dimethyl formamide), nitriles (e.g. acetonitrile), esters (e.g. ethyl acetate), tertiary amines (e.g. triethylamine), nitrogen heterocycles (e.g. pyridine).

Examples of polar protic solvents include water, alcohols, carboxylic acids (e.g. formic acid and acetic acid) or primary and secondary amines.

Preferably, the used polar solvent will be a protic polar solvent and, among them, it will be preferred to use an alcohol.

Among the alcohols that can be used, mention may be made of methanol, ethanol, or even isopropanol, with a preference for ethanol and isopropanol.

The used polar extract of an alga of the *Skeletonema* genus will preferably be a polar extract obtained from a microalga that has undergone a prior cell lysis step.

Such a cell lysis step can be carried out simply by freezing/thawing (preferably at a temperature below −20° C.), by microwave treatment or by ultrasound treatment of this alga.

The polar extract of an alga of the *Skeletonema* genus results from maceration of this alga in the polar solvent for a period of at least 5 minutes, preferably at least 10 minutes. Typically, this maceration time is less than 24 hours, preferably less than 12, or even less than 6 hours. By way of example, such a polar extract of the alga of the *Skeletonema* genus will be obtained by maceration of this alga in the polar solvent for a period comprised between 10 and 60 minutes, preferably between 20 and 40 minutes. Ideally, this maceration with a polar solvent at room temperature or less for preserving as much as possible the photosensitizers of the obtained polar extract.

Still as for this polar extract of an alga of the *Skeletonema* genus, it results from an extraction using at least 1 mL of polar solvent per gram of microalgae (expressed in dry weight), preferably at least 10 mL of polar solvent per gram of microalgae and, particularly preferably at least 20 mL of polar solvent per gram of microalgae. By way of example, the polar extract of an alga of the *Skeletonema* genus is obtained using between 1 and 200 mL of polar solvent per gram of microalgae (expressed in dry weight), preferably between 10 and 100 mL of polar solvent per gram of microalgae and, particularly preferably between 20 and 50 mL of polar solvent per gram of microalgae (expressed in dry weight).

Advantageously, the polar extract of an alga of the *Skeletonema* genus will have undergone at least one filtration (e.g. 0.2 μm, 0.4 μm or other filter) and/or at least one centrifugation (with recovery of the supernatant alone) following extraction.

"Photosensitizer derived from a polar extract of an algae of the *Skeletonema* genus" refers to a compound purified from a polar extract of an algae of the *Skeletonema* genus (for example by HPLC) or to a compound present in a polar extract of an alga of the *Skeletonema* genus which, when activated by light, allows the production of singlet oxygen and R.O.S.

The extract content of an algae of the *Skeletonema* genus in the composition for a photodynamic treatment is comprised between 0.001% and 5% (by dry weight of extract relative to the total weight of the composition), preferably between 0 0.01% and 2% and, particularly preferably between 0.1% and 1%.

During the preparation of the composition of the invention, the integration of the polar extract will preferably take place under an inert atmosphere (e.g. nitrogen or argon) and/or in the dark. Such integration conditions make it possible to best protecting the active molecules of the extract.

Regarding the form of the composition, it can take any desirable form depending on the desired mode of administration. Now, the composition is preferably applied to an epithelium surface like the skin. Also, it will preferably take the form of a dermatological composition such as an ointment, a cream, a lotion or even a gel.

Preferably, the composition may also comprise at least one antioxidant. By way of example of an antioxidant agent which can be used in such a composition, mention may be made of provitamins A, vitamin C, vitamin E, polyphenols or else lycopene. We will preferably opt for a provitamin A, vitamin C or vitamin E.

Now and in general, this composition may include many types of adjuvants or active ingredients used in pharmaceutical or cosmetic formulations, preferably dermatological, whether fatty substances, organic solvents, thickeners, gelling agents, softeners, antioxidants, opacifiers, stabilizers, foaming surfactants and/or detergents, emollients, superfatting agents, perfumes, ionic or non-ionic emulsifiers, fillers, sequestrants, chelators, preservatives, essential oils, coloring matter, pigments, hydrophilic or lipophilic active agents, humectants, such as for example glycerin or glycols, preservatives, dyes, cosmetic active agents, mineral and/or organic sunscreens, mineral fillers, synthetic fillers, silicone elastomers, or plant extracts or even lipid vesicles, or any other ingredient usually used in cosmetic.

Examples of oils include paraffins, isoparaffins, white mineral oils, vegetable oils (from flowers, fruits, vegetables, trees, cereals, oilseeds . . . ), animal oils, synthetic oils, silicone oils and fluorinated oils; and more particularly: oils of plant origin, such as sweet almond oil, coconut oil, castor oil, jojoba oil, olive oil, rapeseed oil, peanut oil, sunflower oil, wheat germ oil, corn germ oil, soybean oil, cottonseed oil, alfalfa oil, 1 poppyseed oil, pumpkin oil, evening primrose oil, millet oil, barley oil, rye oil, safflower oil, bankoulier oil, passionflower oil, hazelnut oil, palm oil, shea butter, apricot kernel oil, calophyllum oil, seedwort oil, avocado oil, calendula oil, oils from flowers or vegetables; ethoxylated vegetable oils; oils of animal origin, such as squalene, squalane; mineral oils, such as paraffin oil, petroleum jelly and isoparaffins; synthetic oils, in particular fatty acid esters such as butyl myristate, propyl myristate, cetyl myristate, isopropyl palmitate, butyl stearate, hexadecyl stearate, isopropyl stearate, octyl stearate, isocetyl stearate, dodecyl oleate, hexyl laurate, propylene glycol dicaprylate; esters derived from lanolic acid, such as isopropyl lanolate, isocetyl lanolate, monoglycerides, diglycerides and triglycerides of fatty acids such as glycerol triheptanoate, alkylbenzoates, polyalphaolefins, polyolefins such as polyisobutene, synthetic isoalkanes such as isohexadecane, isododecane, perfluorinated oils and silicone oils. Among the latter, mention may more particularly be made of dimethylpolysiloxanes, methylphenylpolysiloxanes, silicones modified with amines, silicones modified with fatty acids, silicones modified with alcohols, silicones modified with alcohols and fatty acids, silicones modified with polyether groups, modified epoxy silicones, silicones modified with fluorinated groups, cyclic silicones and silicones modified with alkyl groups.

As other fats, mention may be made of fatty alcohols, linear or branched, saturated or unsaturated, mixtures of fatty alcohols, linear and/or branched, saturated and/or unsaturated, or fatty acids, linear or branched, saturated or unsaturated, mixtures of linear or branched, saturated or unsaturated fatty acids.

Among the thickening and/or emulsifying polymers that can be used, there are, for example, homopolymers or copolymers of acrylic acid or derivatives of acrylic acid, homopolymers or copolymers of methacrylic acid or derivatives of methacrylic acid, homopolymers or copolymers of acrylamide, homopolymers or copolymers of acrylamide derivatives, homopolymers or copolymers of acrylamidomethyl propanesulfonic acid, homopolymers or copolymers of vinyl monomers, homopolymers or copolymers of trimethylaminoethylacrylate, hydrocolloids of plant or biosynthetic origin such as for example xanthan gum, karaya gum, carrageenans, alginates; silicates; cellulose and its derivatives; starch and its hydrophilic derivatives; polyurethanes.

Among the polyelectrolyte-type polymers that can be used in the production of a gelled aqueous phase suitable for use in the preparation of W/O, O/W, W/O/W or O/W/O emulsions, or an aqueous gel comprising SEPIBIO™ POTENTILLA 217, there are, for example, copolymers of acrylic acid and 2-methyl-[(1-oxo-2-propenyl) amino acid] 1-propane sulfonic acid (AMPS), copolymers of acrylamide and 2-methyl-[(1-oxo-2-propenyl)amino] 1-propane sulfonic acid, 2-acid copolymers-methyl-[(1-oxo-2-propenyl) amino] 1-propane sulfonic acid and (2-hydroxyethyl) acrylate, the homopolymer of 2-methyl-[(1-oxo-2-propenyl) amino] 1-propanesulfonic acid, homopolymer of acrylic acid, copolymers of acryloyl ethyl trimethyl ammonium chloride and acrylamide, copolymers of AMPS and vinylpyrolidone, copolymers of 1 'AMPS and N,N-dimethylacrylamide, the terpolymers of AMPS, acrylic acid and N,N-dimethyla crylamide, copolymers of acrylic acid and alkyl acrylates whose carbon chain comprises between ten and thirty carbon atoms, copolymers of AMPS and alkyl acrylates whose carbon chain comprises between ten and thirty carbon atoms.

Among the waxes that can be used in the compositions according to the invention, mention may be made, for example, of beeswax, carnauba wax, Candelilla wax, Ouricoury wax, Japanese wax, China, rice bran wax, Montan wax, cork fiber or sugar cane wax, paraffin waxes, lignite waxes, microcrystalline waxes, lanolin wax, ozokerite, polyethylene wax, hydrogenated oils, silicone waxes, alkenone waxes, vegetable waxes, fatty alcohols and fatty acids solid at room temperature, glycerides solid at room temperature.

Among the emulsifiers that can be used in the compositions according to the invention, mention may be made of:

- fatty esters of alkylpolyglycosides optionally alkoxylated;
- alkoxylated fatty esters;
- polyalkylene glycol carbamates with fatty chains;
- fatty acids, ethoxylated fatty acids, fatty acid sorbitol esters, ethoxylated fatty acid esters, polysorbates, polyglycerol esters, ethoxylated fatty alcohols, sucrose esters, alkylpolyglycosides, alcohols sulfated and phosphated fats or mixtures of alkylpolyglycosides and fatty alcohols;
- combinations of emulsifying surfactants chosen from alkylpolyglycosides;
- associations of alkylpolyglycosides and fatty alcohols, esters of polyglycerols or polyglycols or polyols.

Among the surfactants that can be used in the compositions according to the invention, mention may be made of topically acceptable anionic, cationic, amphoteric or nonionic surfactants usually used in this field of activity.

Among the anionic surfactants that can be used in the compositions according to the invention, particular mention will be made of alkali metal salts, alkaline-earth metal salts, ammonium salts, amino acid salts, aminoalcohol salts of the following compounds: alkylether sulphates, alkylsulphates, alkylamidoethersulphates, alkylarylpolyethersulphates, monoglyceride sulphates, alpha-olefin sulphonates, paraffin sulphonates, alkylphosphates, alkyletherphosphates, alkylsulphonates, alkylamidesulphonates, alkylarylsulphonates, alkylcarboxylates, alkylsulfosuccinates, alkylethersulfosuccinates, alkylamidesulfosuccinates, alkylsulfoacetates, alkylsarcosinates, acylisethionates, N-acyltaurates, acyllactylates.

Among the amphoteric surfactants that can be used in the compositions according to the invention, mention may be made of alkylbetaines, alkylamidobetaines, sultaines, alkylamidoalkylsulfobetaines, imidazoline derivatives, phosphobetaines, amphopolyacetates and amphopropionates.

In order to further potentiate the activity obtained by the composition according to the invention, it may be combined with other active ingredients, in particular those known for their anti-ageing, firming, restructuring, stimulating, energizing, anti-wrinkles, moisturizing, antimicrobial, sebum-regulating, purifying, soothing, relaxing, decontracting, anti-stress, brightening, immunomodulating, cell renewal stimulating, lifting, plumping, improving the radiance of the complexion, etc.

Regarding the light exposure of the area to be treated allowing the activation of the photosensitizer present in this extract, it is an exposure to a light wave having a wavelength comprised between 400 and 800 nm, preferably between 450 and 700 nm, and an intensity (fluence) of between 1 $J/cm^2$ and 100 $J/cm^2$, preferably between 1 and 10 $J/cm^2$.

Such a light wave can be obtained by means of a laser, pulsed-light, or even LEDs. In the context of therapeutic and, in particular, dermatological use, the use of LEDs will be preferred in view of the absence of heating undergone by the cells of the subject so as to limit the damage suffered by his dermis and his epidermis. Now, such a light wave may possibly also correspond to daylight.

The exposure time will be comprised between 1 minute and 2 hours, preferably between 1 and 30 minutes, or even between 1 and 10 minutes and, particularly preferably between 2 and 5 minutes.

The demonstration of a photosensitizing activity associated with the polar extract of *Skeletonema* makes it possible to use it in any type of photodynamic treatment (PDT).

"Photodynamic treatment" means treatment by light exposure of the composition, after it has been applied, for allowing the activation of the photosensitizer present in the polar extract of an alga of the *Skeletonema* genus.

Multiple photodynamic treatments are possible, such as the treatment of acne, the treatment of bacterial infections of the skin or gums, the treatment of hirsutism by destroying the follicles, the treatment of baldness by stimulation of the scalp in areas of hair loss, treatment of inflammatory keratoses, treatment of pre-melanoma dermal areas, treatment of psoriasis, treatment of benign skin conditions such as port wine stains, warts, treatment of different forms of hydradenitis such as hydradenitis suppurativa, Verneuil's disease, or even anti-angiogenic treatment, in particular that of rosette.

Preferably, the dermatological composition is aimed at the treatment of acne in a subject by the topical application of the composition to a skin surface of the subject in combination with a light exposure of this skin surface for allowing the activation of the photosensitizer present in the extract.

In connection with acne, this can correspond just as well to acne vulgaris, to polymorphic acne, to nodulocystic acne, to acne conglobata as to secondary acne (ex. solar acne or acne associated with a treatment).

Now, the composition according to the invention can also target the prevention and/or the treatment of a bacterial infection in a subject by the topical application of the composition on a surface of the subject's epithelium in combination with an exposure light of this epithelium surface for allowing the activation of the photosensitizer present in the extract.

By way of example, we can notably cite the prevention or treatment of gingivitis (inflammation of the gums following a bacterial infection) or periodontitis (inflammation of the periodontium following a bacterial inflammation), the prevention of a skin bacterial infection such as perleche, intertrigo, erysipelas, impetigo, or felon.

Preferably, the bacterial infection is a Gram-positive bacterial infection.

The epithelium surface on which the dermatological composition is applied may correspond to the gums (gingivitis or periodontitis) or even to a skin surface, such as the face, the trunk, the legs, the back or the fingers, preferably to the face.

As for the subject, it is a mammal, preferably a human.

In the case of acne treatment, the subject will typically be between 10 and 20 years old. Now, the acne appearance can be around 7-8 years old and persist after 20 years, the subject can be younger than 10 years old and older than 20 years old.

The composition according to the invention is applied to the affected epithelium surface (skin, gums, etc.) at least once a day.

The combination of the application of the composition according to the invention and of the light exposure is carried out for at least one week to obtain the best effectiveness and, preferably over a period comprised between 4 and 12 weeks.

In connection with the photodynamic treatment method according to the invention, the latter naturally uses the composition as described above.

The photodynamic treatment corresponds to one of the treatments considered above.

Advantageously, the method according to the invention aims to prevent and/or treat acne in a subject.

Still advantageously, the method according to the invention aims to prevent and/or treat a bacterial infection in a subject.

"Therapeutically effective amount" means an amount sufficient to achieve the desired biological effect.

In connection now with the cosmetic treatment method according to the invention, the latter also uses the composition as described above.

For this one, the subject is as previously envisaged.

Advantageously, this aims to eliminate blackheads.

Now, concerning the kit according to the invention, this comprises, in addition to the composition as described above, a light source capable of inducing the activation of the photosensitizer present in the algae extract.

Typically, such a light source emits a light radiation having a wavelength comprised between 400 and 800 nm, preferably between 450 and 700 nm, with an intensity (fluence) comprised between 1 $J/cm^2$ and 100 $J/cm^2$, preferably between 1 and 10 $J/cm^2$.

Such a light source is typically chosen from a laser, a pulsed-light, or even a LED, preferably between a pulsed-light and a LED.

Turning now to the methods for decontaminating a surface, this can be aimed at food (agri-food) or hospital use. In the medical field, it is possible for the sterilization of medical devices, prostheses, implants or other. In the food industry, it can then be used for the decontamination of a food surface (meat, fish, etc.) and we will then speak of conservation, the decontamination of a metal surface (machine, work plan, etc.), or that of a floor or a wall.

In the case of the method according to the invention, it is preferable to use a formulation of the extract allowing it to be vaporized on the surface to be decontaminated. As such, a formulation of the spray type constitutes a particularly suitable formulation.

The invention will be better understood in the light of the following examples, which are given for purely illustrative purposes and are not intended to limit the scope of the invention defined by the appended claims.

EXAMPLES

Example 1: Obtaining a Polar Extract of an Algae of *Skeletonema* Genus

Preferably, all of the extraction is carried out under an inert atmosphere (nitrogen saturation) in order to avoid a pronounced degradation of the active molecules.

For this extraction, we use 10 grams of biomass (*Skeletonema marinoï, S. grethae*, S. *subsalsum* or *S. menzelii*).

Preferably, the algae are frozen at −20° C. before being immersed in 400 mL of ethanol with stirring at room temperature for at least one hour (typically 4 hours).

After this maceration step, the extract is then centrifuged to remove the pellet containing in particular the silica, then the supernatant is filtered (e.g. 0.2 μm filter).

Finally, an extract is obtained with about 40 ml per gram of material.

The polar extract thus obtained is then analyzed by HPLC chromatography (UV-DAD) using a C18 column. The elution gradient used, at a flow rate of 1 mL/min, is presented in Table 1 below.

TABLE 1

| Time (min) | % Methanol/water (80/20) | % Acetonitrile/ water(90/10) | % Ethyl acetate (100) |
|---|---|---|---|
| 0 | 100 | 0 | 0 |
| 3 | 0 | 100 | 0 |
| 35 | 0 | 30 | 70 |
| 38 | 0 | 0 | 100 |
| 41 | 0 | 0 | 100 |
| 43 | 0 | 100 | 0 |
| 45 | 100 | 0 | 0 |
| 47 | 100 | 0 | 0 |

The absorbance analysis of the elution fractions shows numerous absorbance peaks.

Example 2: Antibacterial Action of a Polar Extract of an Algae of the *Skeletonema* Genius The antibacterial activity of the obtained *S. marinoï* polar extract is evaluated by means of an agar diffusion test on the following strains: Cutibacterium *acnes* (CIP 53.117T), *Staphylococcus aureus* (CIP76.25), *Staphylococcus epidermidis* (CIP109.562).

For each strain, a tenfold dilution of a bacterial suspension taken during the exponential growth phase is carried out. 1 mL of diluted bacterial suspension is inoculated onto nutrient agar in a Petri dish, then deposit zones are created in the agar.

These drop zones are filled with:

50 μl of polar extract twenty-fold dilution

50 μl of polar extract two-fold dilution

50 μl of gentamicin, as a witness to the proper functioning of the test, the antibiotic having proven biological activity on the tested strains 50 μl of nutrient medium, supplemented with ethanol as a solvent control (noted "Et5%").

After depositing the solutions, the Petri dishes are subjected or not to illumination with light sources delivering either white light (total fluence of 25 J/cm$^2$) or red light (total fluence of 37.5 J/cm$^2$). A no-illumination condition is performed to determine whether the extract has an antibacterial activity (toxicity) or not, in the absence of illumination.

The antibacterial activity is revealed by the presence of a growth inhibition zone around the sample deposit areas.

The results under white light are presented in Table 2 below.

TABLE 2

| | | Inhibition of bacterial growth | | |
|---|---|---|---|---|
| | | *C. acnes* | *S. aureus* | *S. epidermidis* |
| With illumination | Polar extract ½ | ++ | ++ | ++ |
| | Polar extract 1/20$^{ème}$ | + | + | + |
| | Gentamicin | ++ | ++ | +++ |
| | Solvent control | − | − | − |
| Without illumination | Polar extract ½ | +/− | +/− | +/− |
| | Polar extract 1/20$^{ème}$ | − | − | − |
| | Gentamicin | ++ | ++ | ++ |
| | Solvent control | − | − | −[w1] |

The results under red light are shown in Table 3 below.

TABLE 3

| | | Inhibition of bacterial growth | | |
|---|---|---|---|---|
| | | *C. acnes* | *S. aureus* | *S. epidermidis* |
| With illumination | Polar extract ½ | ++ | + | ++ |
| | Polar extract 1/20$^{ème}$ | + | + | + |
| | Gentamicin | + | +++ | +++ |
| Without illumination | Polar extract ½ | + | +/− | +/− |
| | Polar extract 1/20$^{ème}$ | − | − | − |
| | Gentamicin | ++ | ++ | +++ |

As expected, the results show a bacterial growth inhibition zone for each strain with gentamicin, whether without illumination or with illumination with white or red light. Similarly, no inhibition of bacterial growth is observed in connection with the negative control, whether with or without illumination. As for the polar extract of the algae *Skeletonema marinoï*, little or no inhibition of bacterial growth is observed in the absence of illumination. On the other hand, an inhibition of the bacterial growth of *S. aureus*, *S. epidermidis* and C. *acnes* is observed, which is all the stronger as the extract is less diluted.

In conclusion, the results show that the polar extract does not possess antibiotic activity or toxicity against bacterial models into darkness. On the other hand, the extract is photoactivatable since it generates growth inhibition zones in both white and red light. In addition, there is a dose effect since a greater growth inhibition zone is observed with the extract diluted to 1/20 compared to the extract diluted to ½.

Example 3: Determination of the MIC (Minimum Inhibitory Concentration) and of the MBC (Minimum Bactericidal Concentration) of a polar extract of an algae of the *Skeletonema* Genus The MIC and the MBC of the *S. marinoï*, *S. grethae*, *S. subsalsum* and *S. menzelii* polar extracts were determined in a 96-well plate by a micromethod. The MIC (Minimum Inhibitory Concentration) of an extract corresponds to the smallest concentration of polar extract sufficient to inhibit the growth of a bacterial strain. The MBC (Minimum Bactericidal Concentration) of the extract corresponds to the lowest concentration of extract sufficient to kill 99.99% of the bacteria in the initial inoculum. The bacteria (*C. acnes*, *S. aureus*, *S. epidermidis*) in the exponential phase of growth are incubated in the presence of different concentrations of a polar extract. The bacteria in the presence of the polar extract are then subjected to illumination, either white light (total fluence of 25 J/cm$^2$), or red light (total fluence of 37.5 J/cm$^2$). A condition without illumination is performed to determine whether the tested polar extract has antibacterial activity (toxicity) or not, in the absence of illumination (darkness). After the illumination period, the 96-well plates are then incubated in an oven respecting the optimal conditions for bacteria growth.

The results of the MICs and MBCs under white light are shown respectively in Tables 4 and 5 below. The MIC and MBC values are expressed in µg/mL of polar extract.

TABLE 4

| | MIC (µg/mL) | | | |
|---|---|---|---|---|
| | *S. marinoï* | *S. grethae* | *S. subsalsum* | *S. menzelii* |
| *S. aureus* | 62.5 | 31 | 125 | 250 |
| *S. epidermidis* | 16 | 63 | 16 | 63 |
| *C. Acnes* | 6.25 | 6 | 16 | 31 |

TABLE 5

| | MBC (µg/mL) | | | |
|---|---|---|---|---|
| | *S. marinoï* | *S. grethae* | *S. subsalsum* | *S. menzelii* |
| *S. aureus* | 62.5 | 1000 | >1000 | >1000 |
| *S. epidermidis* | 31 | >1000 | 250 | >1000 |
| *C. Acnes* | 6.25 | n.d. | n.d. | n.d. |

The results of the MIC and MBC under red light are respectively presented in tables 6 and 7 below. The MIC and MBC values are expressed in µg/ml of polar extract.

TABLE 6

| | MIC (µg/mL) | | | |
|---|---|---|---|---|
| | *S. marinoï* | *S. grethae* | *S. subsalsum* | *S. menzelii* |
| *S. aureus* | 125 | 125 | >1000 | >1000 |
| *S. epidermidis* | 63 | 250 | 125 | 250 |
| *C. Acnes* | 125 | 500 | 1000 | >1000 |

TABLE 7

| | MBC(µg/mL) | | | |
|---|---|---|---|---|
| | *S. marinoï* | *S. grethae* | *S. subsalsum* | *S. menzelii* |
| *S. aureus* | 1000 | >1000 | >1000 | >1000 |
| *S. epidermidis* | >1000 | >1000 | >1000 | >1000 |
| *C. Acnes* | <1000 | n.d. | n.d. | n.d. |

The results of the MIC and MBC without illumination are presented in Tables 8 and 9 below. The MIC and MBC values are expressed in µg/mL of polar extract.

TABLE 8

| | MIC (µg/mL) | | | |
|---|---|---|---|---|
| | *S. marinoï* | *S. grethae* | *S. subsalsum* | *S. menzelii* |
| *S. aureus* | 250 | 250 | >1000 | >1000 |
| *S. epidermidis* | 250 | 250 | 250 | 250 |
| *C. Acnes* | <1000 | >1000 | >1000 | >1000 |

TABLE 9

| | MBC (µg/mL) | | | |
|---|---|---|---|---|
| | *S. marinoï* | *S. grethae* | *S. subsalsum* | *S. menzelii* |
| *S. aureus* | <1000 | >1000 | >1000 | >1000 |
| *S. epidermidis* | <1000 | >1000 | >1000 | >1000 |
| *C. Acnes* | <1000 | n.d. | n.d. | n.d. |

The results confirm that the photosensitizers of the polar extract of *Skeletonema* are responsible for the inhibition of bacterial growth observed and, also, of the bacterial lysis observed especially with the extract of *S. marinoï* (Tables 4 and 5 versus Tables 8 and 9). Now, however, it seems that other compounds in these extracts also contribute, but slightly, to the inhibition of the growth of *S. aureus* and *S. epidermidis* bacteria (cf. [Table 8]).

Example 4: In Vitro Evaluation of the Anti-Inflammatory Effect of the Polar Algae Extract of *S. marinoï*

4.1 Method

The anti-inflammatory properties of *S. marinoï* polar algae extract were evaluated on normal human epidermal keratinocytes (NHEK)

These NHEK human epidermal keratinocytes were seeded in K-SFM medium supplemented with 0.25 ng/ml of EGF (Epidermal Growth Factor), 25 µg/mL of pituitary extract and 25 µg/mL of Gentamycin in 96-well plates to then be incubated at 37° C. under an atmosphere containing 5% CO2. After at least one day of culturing, the NHEK cells are pre-incubated for 24 hours in the presence or absence of different concentrations of the *S. marinoï* polar extract. As a positive control of anti-inflammatory activity, NHEK cells were also pre-incubated in the presence of bafilomycin (100 nM). After this pre-incubation, the treatments were renewed and the NHEK cells are then incubated for 24 hours in the presence of poly (I:C) for inducing inflammation. A control condition without inflammation inducer (unstimulated control) was performed in parallel.

After incubation, the culture supernatant was collected to determine the level of keratinocyte inflammation by ELISA by measuring the amounts of IL-6 secreted.

4.2 Results

TABLE 10

| | IL6 (pg/mL) (inhibition %) | Cell viability (WST-8) |
|---|---|---|
| Unstimulated cells (control) | <9 (100) | 124 |
| Cells stimulated with Poly(I:C) 1 (µg/mL) without treatment | 1495 (0) | 100 |
| Cells stimulated with Poly(I:C) 1 (µg/mL) + Bafilomycin 100 nM (positive reference) | 13 (100) | 100 |
| NHEK cells stimulated with Poly(I:C) 1 (µg/mL) + *S. marinoï* polar algae extract (10 µg/mL)) | 1243 (17) | 67 |

4.3 Interpretation and Conclusions

As expected, stimulation of NHEK cells with 1 µg/mL of Poly (I:C) induces strong production of the pro-inflammatory cytokine IL-6 compared to unstimulated cells (IL6:

1495 vs <9). In the presence of 100 nM Bafilomycin, the effect of Poly (I:C) on NHEK cells is completely inhibited (positive reference).

It is found that the extract of polar algae *S. marinoï* induces a weak inhibition (17%), but significant, on the release of pro-inflammatory cytokine IL-6 induced by Poly (I:C) when the stimulated NHEK cells are treated with an extract of concentration equal to 10 μg/mL.

Example 5: In Vitro Evaluation of the Anti-Lipogenic Effect of the Polar Algae Extract of *S. marinoï*

5.1 Method

The effect of *S. marinoï* polar algae extract on the overproduction of lipids was studied on human sebocytes of the SEBO662AR line (BIOALTERNATIVES line) stimulated by lipogenic and androgenic factors.

SEBO662AR human sebocytes were first cultured at 37° C. in the presence of 5% CO2 and antibiotics in a dedicated culture medium. After at least one day of culturing, lipogenesis is induced in the SEBO662AR cells by their incubation in the presence of lipogenic and androgenic factors. The cells are then incubated in the presence or in the absence of 3 distinct concentrations of the polar extract. As a positive control of lipogenesis inhibitory activity, the SEBO662AR cells are incubated in the presence of cerulenin. At the end of the incubation period, the total lipids are fluorescently labelled, and the inhibition of lipogenesis is determined for each condition.

5.2 Results

TABLE 7

| | Lipids (BODIPY ® probe) Fluorescence intensity/ Number of nuclei | Stimulation % | Relative inhibition % |
|---|---|---|---|
| Unstimulated cells (control) | 7 895*** | 3 | 100*** |
| Cells stimulated with a lipogenic mixture containing androgens without treatment | 298 525 | 100 | 0 |
| Cells stimulated with a lipogenic mixture containing androgens + Cerulenin 10 μM (positive reference) | 188 853** | 63 | 38** |
| Cells stimulated with a lipogenic mixture containing androgens + *S. marinoï* polar algae extract (10 μg/mL) | 151 191* | 51 | 51*** |
| Cells stimulated with a lipogenic mixture containing androgens + *S. marinoï* polar algae extract (5 μg/mL) | 187 489 | 63 | 38** |
| Cells stimulated with a lipogenic mixture containing androgens + *S. marinoï* polar algae extract (1 μg/mL) | 238 893* | 80 | 21* |

***: $p < 0.001$ (extremely significant);
**: $0.001 \leq p \leq 0.01$ (very significant);
*: $p > 0.05$ (non-significant)

5.3 Interpretation and Conclusions

As expected, stimulation of SEBO662AR sebocytes by a lipogenic mixture, containing androgens, causes the formation and accumulation of lipid droplets compared to unstimulated sebocytes (fluorescence intensity/number of nuclei: 298525 versus 7895).

The measurements recorded in Table 7 show that treatment of stimulated cells with *S. marinoï* polar algae extract at 10 μg/mL makes it possible to inhibit the production of lipids by 51% compared to stimulated and not treated cells. By way of comparison, treatment of these same cells with cerulenin (positive control) inhibits lipid production by only 38% compared to stimulated and untreated cells. The measurements recorded in Table 7 show that the lipogenesis-inhibiting effect induced by the *S. marinoï* polar algae extract is dose-dependent. A two-fold reduction of the extracts concentration generates a 38% inhibition; and a ten-fold reduction generates a 21% inhibition of 21%.

Finally, it should be noticed that the polar algae extract of *S. marinoï* has no effect on cell viability. Indeed, counting the number of nuclei per field indicates a globally comparable number of nuclei for all the tested conditions. In addition, no morphological alteration could be observed during microscopic observations carried out at the end of incubation. It follows that the inhibitory effect of the *S. marinoï* polar algae extract on lipogenesis is specific and not linked to an associated partial cytotoxicity phenomenon.

The invention claimed is:

1. A photodynamic treatment method to prevent or treat acne or a bacterial infection in a subject, the method comprising:

topically applying epithelium surface of the subject a therapeutically effective amount of a composition comprising at least one polar extract of an alga of the *Skeletonema* genus or a photosensitizer derived therefrom; and exposing the epithelium surface to light to activate the photosensitizer;

wherein the method is performed to treat acne.

2. The method according to claim 1, wherein the alga of the *Skeletonema* genus is chosen from the group comprising *Skeletonema ardens, Skeletonema barbadense, Skeletonema costatum, Skeletonema cylindraceum, Skeletonema denticulatum, Skeletonema dohrnii, Skeletonema grethae, Skeletonema grevillei, Skeletonema japonicum, Skeletonema marinoi, Skeletonema mediterraneum, Skeletonema menzelii, Skeletonema mirabile, Skeletonema potamos, Skeletonema probabile, Skeletonema pseudocostatum, Skel-*

*etonema simbirskianum Skeletonema subsalum, Skeletonema tropicum, Skeletonema utriculosa* and *Skeletonema ventricosum.*

3. The method according to claim 2, wherein the alga of the *Skeletonema* genus is chosen from the group comprising *Skeletonema costatum, Skeletonema grethae, Skeletonema marinoi, Skeletonema menzellii* and *Skeletonema subsalsum.*

4. The method according to claim 1, wherein the polar extract of an alga of the *Skeletonema* genus is obtained by an extraction carried out with an alcohol.

5. The method according to claim 1, wherein the extract content of an alga of the *Skeletonema* genus in the dermatological composition for the treatment of acne is between 0.001% and 5% by extract dry weight relative to the total weight of the composition.

6. The method according to claim 1, wherein the light exposure of the area to be treated for allowing the activation of the photosensitizer present in this extract corresponds to an exposure to a light wave having a length wave between 400 and 800 nm.

7. The method according to claim 1, wherein the light exposure of the area to be treated for allowing the activation of the photosensitizer present in this extract corresponds to an exposure to a light wave having an intensity comprised between 1 $J/cm^2$ and 100 $J/cm^2$.

8. The method of claim 4, wherein the alcohol is ethanol or isopropanol.

9. The method of claim 5, wherein the extract content of an alga of the *Skeletonema* genus in the dermatological composition for the treatment of acne is between 0.01% and 1% by extract dry weight relative to the total weight of the composition.

10. The method of claim 6, wherein the light exposure of the area to be treated for allowing the activation of the photosensitizer present in this extract corresponds to an exposure to a light wave having a length wave between 450 and 700 nm.

11. The method of claim 7, wherein the light exposure of the area to be treated for allowing the activation of the photosensitizer present in this extract corresponds to an exposure to a light wave having an intensity comprised between 1 and 10 $J/cm^2$.

12. The method according to claim 2, wherein the polar extract of an alga of the *Skeletonema* genus is obtained by an extraction carried out with an alcohol.

13. The method according to claim 3, wherein the polar extract of an alga of the *Skeletonema* genus is obtained by an extraction carried out with an alcohol.

14. The method according to claim 2, wherein the extract content of an alga of the *Skeletonema* genus in the dermatological composition for the treatment of acne is between 0.001% and 5% by extract dry weight relative to the total weight of the composition.

15. A cosmetic method for removing blackheads comprising the steps of:

a) topical application to an epithelium surface of a subject of an effective amount of a composition comprising at least one polar extract of an alga of the *Skeletonema* genus or a photosensitizer derived therefrom; and b) light exposure of this epithelium surface for allowing the activation of the photosensitizer.

* * * * *